(12) United States Patent
Chan et al.

(10) Patent No.: US 8,709,355 B2
(45) Date of Patent: *Apr. 29, 2014

(54) MICROFLUIDIC SYSTEM INCORPORATING A METAL IMPREGNATED NANOPOROUS MATERIAL IN A MICROFLUIDIC PATHWAY THEREOF

(71) Applicants: Selena Chan, San Jose, CA (US); Sunghoon Kwon, Albany, CA (US); Narayan Sundararajan, San Francisco, CA (US)

(72) Inventors: Selena Chan, San Jose, CA (US); Sunghoon Kwon, Albany, CA (US); Narayan Sundararajan, San Francisco, CA (US)

(73) Assignee: Intel Corporation, Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/730,431

(22) Filed: Dec. 28, 2012

(65) Prior Publication Data
US 2013/0243656 A1 Sep. 19, 2013

Related U.S. Application Data (60) Continuation of application No. 12/575,369, filed on Oct. 7, 2009, now Pat. No. 8,367,017, which is a division of application No. 11/436,489, filed on May 18, 2006, now Pat. No. 7,608,305, which is a division of application No. 10/368,976, filed on Feb. 18, 2003, now Pat. No. 7,361,313.

(51) Int. Cl.
*G01N 21/65* (2006.01)
*G01J 3/44* (2006.01)

(52) U.S. Cl.
USPC ......... 422/502; 356/301; 422/82.05; 436/164

(58) Field of Classification Search
USPC ................ 148/240; 356/301; 422/82.05, 502; 436/2, 5, 164, 171, 183; 438/589
See application file for complete search history.

(56) References Cited

U.S. PATENT DOCUMENTS 1,988,012 A * 1/1935 Bryant ........................ 148/272
3,702,259 A * 11/1972 Nielson ........................ 427/229

(Continued)

FOREIGN PATENT DOCUMENTS

| EP | 0984269 | 3/2000 |
| GB | 0590479 | 7/1947 |

(Continued)

OTHER PUBLICATIONS

Lee, Y.-H. et al., Journal of Raman Spectroscopy 1997, 28, 635-639.

(Continued)

*Primary Examiner* — Arlen Soderquist (57) ABSTRACT

The methods, systems 400 and apparatus disclosed herein concern metal 150 impregnated porous substrates 110, 210. Certain embodiments of the invention concern methods for producing metal-coated porous silicon substrates 110, 210 that exhibit greatly improved uniformity and depth of penetration of metal 150 deposition. The increased uniformity and depth allow improved and more reproducible Raman detection of analytes. In exemplary embodiments of the invention, the methods may comprise oxidation of porous silicon 110, immersion in a metal salt solution 130, drying and thermal decomposition of the metal salt 140 to form a metal deposit 150. In other exemplary embodiments of the invention, the methods may comprise microfluidic impregnation of porous silicon substrates 210 with one or more metal salt solutions 130. Other embodiments of the invention concern apparatus and/or systems 400 for Raman detection of analytes, comprising metal-coated porous silicon substrates 110, 210 prepared by the disclosed methods.

11 Claims, 5 Drawing Sheets

(56) References Cited

U.S. PATENT DOCUMENTS

| | | | |
|---|---|---|---|
| 3,725,307 A | 4/1973 | Brown et al. | |
| 3,883,307 A | 5/1975 | Kim | |
| 3,932,548 A * | 1/1976 | Rausch | 585/434 |
| 4,097,414 A * | 6/1978 | Cavitt | 502/347 |
| 4,102,820 A * | 7/1978 | Cavitt | 502/348 |
| 4,248,741 A * | 2/1981 | Wernli et al. | 502/341 |
| 4,303,612 A | 12/1981 | Sonley | |
| 4,801,380 A | 1/1989 | Parker et al. | |
| 5,064,693 A | 11/1991 | Hayakawa et al. | |
| 5,255,067 A | 10/1993 | Carrabba et al. | |
| 5,306,403 A | 4/1994 | Vo-Dinh | |
| 5,561,304 A | 10/1996 | Canham et al. | |
| 5,567,628 A | 10/1996 | Tarcha et al. | |
| 5,733,507 A * | 3/1998 | Zakim | 422/535 |
| 5,770,022 A | 6/1998 | Chang et al. | |
| 5,858,195 A | 1/1999 | Ramsey | |
| 5,874,047 A | 2/1999 | Schoning et al. | |
| 5,961,815 A * | 10/1999 | Hickey et al. | 208/108 |
| 5,994,164 A | 11/1999 | Fonash et al. | |
| 6,002,471 A | 12/1999 | Quake | |
| 6,017,773 A | 1/2000 | Fauchet et al. | |
| 6,040,191 A | 3/2000 | Grow | |
| 6,096,496 A | 8/2000 | Frankel | |
| 6,136,389 A | 10/2000 | Conover et al. | |
| 6,136,704 A | 10/2000 | Maya | |
| 6,149,868 A | 11/2000 | Natan et al. | |
| 6,153,489 A | 11/2000 | Park et al. | |
| 6,171,945 B1 | 1/2001 | Mandal et al. | |
| 6,174,677 B1 | 1/2001 | Vo-Dinh | |
| 6,180,415 B1 | 1/2001 | Schultz et al. | |
| 6,197,503 B1 | 3/2001 | Vo-Dinh et al. | |
| 6,249,080 B1 | 6/2001 | Komoda et al. | |
| 6,263,286 B1 | 7/2001 | Gilmanshin et al. | |
| 6,268,041 B1 | 7/2001 | Goldstein | |
| 6,294,442 B1 | 9/2001 | Kamal | |
| 6,312,768 B1 | 11/2001 | Rode et al. | |
| 6,313,914 B1 | 11/2001 | Roe | |
| 6,322,895 B1 | 11/2001 | Canham | |
| 6,330,193 B1 | 12/2001 | Yu et al. | |
| 6,344,272 B1 | 2/2002 | Oldenburg et al. | |
| 6,358,613 B1 | 3/2002 | Buriak | |
| 6,358,815 B2 | 3/2002 | Maeda | |
| 6,359,276 B1 | 3/2002 | Tu | |
| 6,376,177 B1 | 4/2002 | Poponin | |
| 6,399,177 B1 | 6/2002 | Fonash et al. | |
| 6,406,984 B1 | 6/2002 | Russell et al. | |
| 6,426,126 B1 | 7/2002 | Conover et al. | |
| 6,478,974 B1 | 11/2002 | Lebouitz et al. | |
| 6,504,292 B1 | 1/2003 | Choi et al. | |
| 6,623,977 B1 | 9/2003 | Farquharson et al. | |
| 6,673,644 B2 | 1/2004 | Gole et al. | |
| 6,797,405 B1 | 9/2004 | Coe et al. | |
| 6,806,543 B2 | 10/2004 | Yamakawa et al. | |
| 6,841,290 B2 | 1/2005 | Klitsner et al. | |
| 6,893,816 B1 | 5/2005 | Beattie | |
| 6,902,934 B1 | 6/2005 | Bergh et al. | |
| 6,970,239 B2 | 11/2005 | Chan et al. | |
| 6,972,173 B2 | 12/2005 | Su et al. | |
| 6,989,897 B2 | 1/2006 | Chan et al. | |
| 7,192,703 B2 | 3/2007 | Sun et al. | |
| 7,238,477 B2 | 7/2007 | Su et al. | |
| 7,267,948 B2 | 9/2007 | Vo-Dinh | |
| 7,361,313 B2 | 4/2008 | Chan et al. | |
| 7,442,339 B2 | 10/2008 | Sundararajan et al. | |
| 7,608,305 B2 | 10/2009 | Chan et al. | |
| 7,771,661 B2 | 8/2010 | Chan et al. | |
| 8,367,017 B2 * | 2/2013 | Chan et al. | 422/502 |
| 2002/0020053 A1 | 2/2002 | Fonash et al. | |
| 2002/0142480 A1* | 10/2002 | Natan | 436/171 |
| 2002/0183580 A1* | 12/2002 | Dyroff | 585/654 |
| 2003/0059820 A1 | 3/2003 | Vo-Dinh | |
| 2003/0135997 A1 | 7/2003 | Watanabe et al. | |
| 2003/0231304 A1 | 12/2003 | Chan et al. | |
| 2006/0049356 A1 | 3/2006 | Shen et al. | |

FOREIGN PATENT DOCUMENTS

| | | |
|---|---|---|
| GB | 2373367 | 9/2002 |
| WO | 0037694 | 6/2000 |
| WO | 03106943 | 12/2003 |

OTHER PUBLICATIONS

Szabo, N. J. et al., Applied Spectroscopy 1997, 51, 965-975.
Oldenburg, S. J. et al., Journal of Chemical Physics 1999, 111, 4729-4735.
Mai, L. H. et al., Sensord and Actuators B 2000, 66, 63-65.
Lucht, S. et al., Journal of Raman Spectroscopy 2000, 31, 1017-1022.
Farquharson, S. et al., Space Technology and Applications International Forum 2000, 306-311.
Liu, F. X. et al., Journal of Raman Spectroscopy 2001, 32, 73-77.
Jackson, J. B. et al., Journal of Physical Chemistry B 2001, 105, 2743-2746.
Alieva et al., Physical Status Solidi A, 1999, 175:115-120.
Baltog et al., Romanian in Physics, 2000, 51:823-841.
Baratto et al., Sensors and Actuators B, 2000, 68:74-80.
Cai et al., Direct Formation of Self-Assembled Nanoporous Aluminum Oxide in $SiO_2$ and Si Substrates, Nanotechnology, 2002, 13:627.
Canham, Silicon Quantum Wire Array Fabrication by Electrochemical and Chemical Dissolutionof Wafers, Applied Physics Letters, 1990, 57:1046.
Cai et al., Optical Properties of Ag and Au Nanoparticles Dispersed Within the Pores of Monolithic Mesoporous Silica, J. Nanoparticle Res., 2001, 3:443-453.
Chan et al., Tunable, Narrow, and Directional Luminescence from Porous Silicon Light Emitting Devices, Applied Physics Letters, 1990, 75:274-276.
Collins et al., Porous Silicon: From Luminescence to LEDs, Physics Today, 1997, 50:24-31.
Coulthand et al., Materials Research Society Symposium Proceedings, 1997, 457:161-165.
Coulthand et al., Solid State Communications, 1998, 105:751-754.
Craighead, Science, 2000, 290:1532-1536.
Cullis et al., The Structural and Luminescence Properties of Porous Silicon, J. Applied Physics, 1997, 82:909-965.
Duffy et al., Rapid Prototyping of Microfluidic Systems in Poly (dimethylsiloxand), Anal. Chem., 1998, 70:4975-4984.
Edelberg et al., Visible Luminescence from Nanocrystalline Silicon Films Produced by Plasma Enhanced Chemical Vapor Deposition, Applied Physics Letters, 1996, 68:1415-1417.
Feldheim, Assembly of Metal Nanoparticle Arrays Using Molecular Bridges, The Electrochemical Society Interface, Fall 2001, 22-25.
Gole et al., Patterned Metallization of Porous Silicon from Electroles Solution for Direct Electrical Contact, J. Electrochem Soc., 2000, 147:3785.
Henneke, Porous Silicon: Theories Behind Light Emission, 1996, http://neon.utexas.edu/academic/courses/Fall1997/CH380L/student.papers.ch.html.
Jin et al., Photoinduced Conversion of Silver Nahospheres to Nanoprisms, Science 2001, 294:1901.
Korsunskaya et al., ASDAM 2000, 3rd Int'l Euro Conf. on Adv. Semiconductor Devices and Microsystems Conf Proceedings, Smolenice Castle, Slovak, Oct. 16-18, 2000, pp. 339-342.
Lopez et al., From Porous Silicon One-Dimensional Photonic Band Gap Structures, Applied Physics Letters, 2000, 77:3704-3706.
Lutzen et al., Structure Characteristics of Ultrathin Nanocrystalline Silicon Films Formed by Annealing Amorphous Silicon, J. Vac . Sci. Technology B., 1998, 16:2802-2805.
Pavesi et al., Journal of Applied Physics, 1994, 75:1118-1126.
Petrova-Koch et al., Rapid-Thermal-Oxidized Porous Silicon-the-Superior Photoluminscence Si, Applied Physics Letters, 1992, 61:943.
Sakka et al., Journal of Porous Materials, 2000, 7:397-400.
Schoenfeld et al., Formation of Si Quantum Dots in Nanocrystalline Silicon, Proc. 7th Int'l Conf. on Modulated Semiconductor Structures, Madrid, 1995, pp. 605-608.

(56) References Cited

OTHER PUBLICATIONS

Unai et al., Photovoltaic Properties of a Novel Stain Etched Porous Silicon and its Applications in Photosensitive Devices, Optical Materials, Jun. 2001, 17(1-2):79-82.

Varghese et al., Highly Ordered Nanoporous Alumina Films: Effect of Pore Size and Uniformity on Sensing Performace, J. Mater. Res., 2002, 17:1162-1171.

Vo-Dinh, Surface-Enhanced Raman Spectroscopy Using Metallic Nanostructures, TRAC, Trends in Analytical Chemistry, Aug. 9, 1998, 17(8-9):557-582.

Voldman et al., Ann. Rev. Biomed. Eng., 1999, 1:401-425.

Wang et al., Faguang Xeubao, 1999, pp. 270-273.

Weiping et al., Synthesis and Structural and Optical Properties of Mesoporous Silica Containing Silver Nanoparticles, J. Phys. Condes. Matter, 1997, 9:7257-7267.

Zhao et al., Nanocrystalline Si: a Mterial Constructed by Si Quantum Dots, 1st Int'l Conf. on Low Dimensional Structures and Devices, 1995, pp. 467-471.

Losey et al., Design and Fabrication of Microfluidic Devices for Multiphase Mixing and Reaction, J. Microelectromechanical Systems, vol. 11, No. 6, Dec. 2002, pp. 709-717.

Pap et al., Simultaneous Chemical Silver and Palladium Deposition on Porous Silicon; FESEM, TEM, EDX and XRD Investigation, Applied Surface Science 201, 2002, pp. 56-60.

\* cited by examiner

MICROFLUIDIC SYSTEM INCORPORATING A METAL IMPREGNATED NANOPOROUS MATERIAL IN A MICROFLUIDIC PATHWAY THEREOF

CROSS-REFERENCE TO RELATED APPLICATIONS

This application is a continuation of U.S. application Ser. No. 12/575,369 filed Oct. 7, 2009, now U.S. Pat. No. 8,367, 017, which is a divisional application of U.S. application Ser. No. 11/436,489 filed May 18, 2006, now U.S. Pat. No. 7,608, 305, which is a divisional application of U.S. application Ser. No. 10/368,976 filed Feb. 18, 2003, now U.S. Pat. No. 7,361, 313. The disclosures of the prior applications are considered part of and are incorporated by reference in the disclosure of this application.

BACKGROUND OF THE INVENTION

1. Field of the Invention

The present methods and apparatus relate to the field of metal 150 impregnation into nanoporous materials 110, 210. More particularly, certain embodiments of the invention concern methods of producing metal-coated porous silicon 110, 210.

2. Background Information

The sensitive and accurate detection and/or identification of single molecules from biological and other samples has proven to be an elusive goal, with widespread potential uses in medical diagnostics, pathology, toxicology, biological warfare, environmental sampling, chemical analysis, forensics and numerous other fields. Attempts have been made to use Raman spectroscopy and/or surface plasmon resonance to achieve this goal. When light passes through a tangible medium, a certain amount becomes diverted from its original direction, a phenomenon known as Raman scattering. Some of the scattered light also differs in frequency from the original excitatory light, due to the absorption of light and excitation of electrons to a higher energy state, followed by light emission at a different wavelength. The wavelengths of the Raman emission spectrum are characteristic of the chemical composition and structure of the light absorbing molecules in a sample, while the intensity of light scattering is dependent on the concentration of molecules in the sample.

The probability of Raman interaction occurring between an excitatory light beam and an individual molecule in a sample is very low, resulting in a low sensitivity and limited applicability of Raman analysis. It has been observed that molecules near roughened silver surfaces show enhanced Raman scattering of as much as six to seven orders of magnitude. This surface enhanced Raman spectroscopy (SERS) effect is related to the phenomenon of plasmon resonance, wherein metal nanoparticles exhibit a pronounced optical resonance in response to incident electromagnetic radiation, due to the collective coupling of conduction electrons in the metal. In essence, nanoparticles of gold, silver, copper and certain other metals can function as miniature "antenna" to enhance the localized effects of electromagnetic radiation. Molecules located in the vicinity of such particles exhibit a much greater sensitivity for Raman spectroscopic analysis.

Attempts have been made to exploit SERS for molecular detection and analysis, typically by coating metal nanoparticles or fabricating rough metal films on the surface of a substrate and then applying a sample to the metal-coated surface. However, the number of metal particles that can be deposited on a planar surface is limited, producing a relatively low enhancement factor for SERS and related Raman techniques utilizing such surfaces. A need exists for methods of producing SERS-active substrates with uniform, high densities of Raman-active metal.

Metal impregnated silicon substrates have been proposed as components of various electrical devices, such as field emission electron sources and light emitting diodes. The efficiency of such devices is limited by a lack of uniformity of electrical contacts, resulting from non-homogeneous metal impregnation. A need exists for methods of producing materials with homogeneous metal impregnation for high efficiency electrical devices.

BRIEF DESCRIPTION OF THE DRAWINGS

The following drawings form part of the present specification and are included to further demonstrate certain aspects of the disclosed embodiments of the invention. The embodiments of the invention may be better understood by reference to one or more of these drawings in combination with the detailed description of specific embodiments presented herein.

FIG. 1 illustrates an exemplary, method for producing a metal-coated porous silicon substrate 110 comprising thermal decomposition of a metal salt solution 130.

FIG. 6 shows the SERS emission spectra obtained with PODD silver-coated substrates 110 of different porosities. The various spectra were obtained at average porosities, in order from the lowest trace to the highest trace, of 52%, 55%, 65%, 70% and 77%.

DESCRIPTION OF ILLUSTRATIVE EMBODIMENTS

The following detailed description contains numerous specific details in order to provide a more thorough understanding of the disclosed embodiments of the invention. However, it will be apparent to those skilled in the art that the embodiments of the invention may be practiced without these specific details. In other instances, devices, methods, procedures, and individual components that are well known in the art have not been described in detail herein.

Definitions

As used herein, "a" or "an" may mean one or more than one of an item.

As used herein, the terms "analyte" and "target", refer to any atom, chemical, molecule, compound, composition or aggregate of interest for detection and/or identification. Non-limiting examples of analytes include an amino acid, peptide, polypeptide, protein, glycoprotein, lipoprotein, nucleoside, nucleotide, oligonucleotide, nucleic acid, sugar, carbohydrate, oligosaccharide, polysaccharide, fatty acid, lipid, hormone, metabolite, cytokine, chemokine, receptor, neurotransmitter, antigen, allergen, antibody, substrate, metabolite, cofactor, inhibitor, drug, pharmaceutical, nutrient, prion, toxin, poison, explosive, pesticide, chemical warfare agent, biohazardous agent, radioisotope, vitamin, heterocyclic aromatic compound, carcinogen, mutagen, narcotic, amphetamine, barbiturate, hallucinogen, waste product and/or contaminant. In certain embodiments of the invention, one or more analytes may be labeled with one or more Raman labels.

As used herein, the term "nanocrystalline silicon" refers to silicon that comprises nanometer-scale silicon crystals, typically in the size range from 1 to 100 nanometers (nm). "Porous silicon" 110, 210 refers to silicon that has been etched or otherwise treated to form a porous structure 110, 210.

As used herein, "operably coupled" means that there is a functional interaction between two or more units of an apparatus and/or system. For example, a Raman detector 410 may be "operably coupled" to a computer if the computer can obtain, process, store and/or transmit data on Raman signals detected by the detector 410.

Porous Substrates

Certain embodiments of the invention concern methods for coating porous substrates 110, 210 with a uniform layer of one or more metals 150, such as Raman active metals 150. Although in particular embodiments of the invention the porous substrates 110, 210 disclosed herein are porous silicon substrates 110, 210, those embodiments are not limiting. Any porous substrate 110, 210 that is resistant to the application of heat may be used in the disclosed methods, systems 400 and/or apparatus. In certain embodiments, application of heat to about 300° C., 400° C., 500° C., 600° C., 700° C., 800° C., 900° C. or 1,000° C. is contemplated. In some embodiments of the invention, the porous substrate 110, 210 may be rigid. A variety of porous substrates 110, 210 are known, including but not limited to porous silicon, porous polysilicon, porous metal grids and porous aluminum. Exemplary methods of making porous substrates 110, 210 are disclosed in further detail below.

Porous polysilicon substrates 110, 210 may be made by known techniques (e.g., U.S. Pat. Nos. 6,249,080 and 6,478,974). For example, a layer of porous polysilicon 310, 210 may be formed on top of a semiconductor substrate by the use of low pressure chemical vapor deposition (LPCVD). The LPCVD conditions may include, for example, a pressure of about 20 pascal, a temperature of about 640° C. and a silane gas flow of about 600 seem (standard cubic centimeters) (U.S. Pat. No. 6,249,080). A polysilicon layer may be etched, for example using electrochemical anodization with HF (hydrofluoric acid) or chemical etching with nitric acid and hydrofluoric acid, to make it porous (U.S. Pat. No. 6,478,974). Typically, porous polysilicon 110, 210 layers formed by such techniques are limited in thickness to about 1 μm (micrometer) or less. In contrast, porous silicon 110, 210 can be etched throughout the thickness of the bulk silicon wafer, which has a typical thickness of about 500 μm.

Porous aluminum substrates 110, 210 may also be made by known techniques (e.g., Cai et al., *Nanotechnology* 13:627, 2002; Varghese et al., *J. Mater. Res.* 17:1162-1171, 2002). For example, nanoporous aluminum oxide thin films 110, 210 may be fabricated on silicon or silicon dioxide 120 using an electrochemical-assisted self-assembly process (Cai et al., 2002). The porous aluminum film 110, 210 may be thermally annealed to improve its uniformity (Cai et al., 2002). Alternatively, a thin layer of solid aluminum may be electrochemically anodized in dilute solutions of oxalic acid and/or sulfuric acid to create a nanoporous alumina film 110, 210. (Varghese et al., 2002). The examples disclosed herein are not limiting and any known type of heat resistant porous substrate 110, 210 may be used. Such porous substrates 110, 210 may be uniformly impregnated with one or more metals 150, such as silver, using the methods disclosed herein.

Nanocrystalline Porous Silicon

Nanocrystalline Silicon

Certain embodiments of the invention concern systems 400 and/or apparatus comprising one or more layers of nanocrystalline silicon. Various methods for producing nanocrystalline silicon are known (e.g., Petrova-Koch et al., "Rapid-thermal-oxidized porous silicon—the superior photoluminescent Si," Appl. Phys. Lett. 61:943, 1992; Edelberg, et al., "Visible luminescence from nanocrystalline silicon films produced by plasma enhanced chemical vapor deposition," Appl. Phys. Lett., 68:1415-1417, 1996; Schoenfeld, et al., "Formation of Si quantum dots in nanocrystalline silicon," Proc. 7th Int. Conf. on Modulated Semiconductor Structures, Madrid, pp. 605-608, 1995; Zhao, et al., "Nanocrystalline Si: a material constructed by Si quantum dots," 1st Int. Conf. on Low Dimensional Structures and Devices, Singapore, pp. 467-471, 1995; Lutzen et al., Structural characteristics of ultrathin nanocrystalline silicon films formed by annealing amorphous silicon, J. Vac. Sci. Technology B 16; 2802-05, 1998; U.S. Pat. Nos. 5,770,022; 5,994,164; 6,268,041; 6,294,442; 6,300,193). The methods, systems 400 and apparatus disclosed herein are not limited by the method of producing nanocrystalline silicon and any known method may be used.

Non-limiting exemplary methods for producing nanocrystalline silicon include silicon (Si) implantation into a silicon rich oxide and annealing; solid phase crystallization with metal nucleation catalysts; chemical vapor deposition; PECVD (plasma enhanced chemical vapor deposition); gas evaporation; gas phase pyrolysis; gas phase photopyrolysis; electrochemical etching; plasma decomposition of silanes and polysilanes; high pressure liquid phase reduction-oxidation reactions; rapid annealing of amorphous silicon layers; depositing an amorphous silicon layer using LPCVD (low pressure chemical vapor deposition) followed by RTA (rapid thermal anneal) cycles; plasma electric arc deposition using a silicon anode and laser ablation of silicon (U.S. Pat. Nos. 5,770,022; 5,994,164; 6,268,041; 6,294,442; 6,300,193). Depending on the process, Si crystals of anywhere from 1 to 100 nm or more in size may be formed as a thin layer on a chip, a separate layer and/or as aggregated crystals. In certain embodiments of the invention, a thin layer comprising nanocrystalline silicon attached to a substrate layer may be used.

In various embodiments of the invention, it is contemplated that nanocrystalline silicon may be used to form a porous silicon substrate 110, 210. However, the embodiments are not limited to as to the composition of the starting material, and in alternative embodiments of the invention it is contemplated that other materials may be utilized, provided that the material is capable of forming a porous substrate 110, 210 that can be coated with a metal 150, as exemplified in FIG. 1.

In certain embodiments of the invention, the size and/or shape of silicon crystals and/or pore size in porous silicon 110, 210 may be selected to be within predetermined limits, for example, in order to optimize the plasmon resonant frequency of metal-coated porous silicon 110, 210 (see, e.g., U.S. Pat. No. 6,344,272). Techniques for controlling the size of nanoscale silicon crystals are known (e.g., U.S. Pat. Nos. 5,994,164 and 6,294,442). The plasmon resonant frequency may also be adjusted by controlling the thickness and/or composition of the metal layer 150 coating the porous silicon 110, 210 (U.S. Pat. No. 6,344,272).

Porous Silicon

Certain embodiments of the invention concern systems 400 and/or apparatus comprising a metal-coated porous substrate 110, 210. In various embodiments, the substrate may comprise nanocrystalline porous silicon 110, 210. The substrate is not limited to pure silicon, but may also comprise silicon nitride, silicon oxide, silicon dioxide 120, germanium and/or other materials known for chip manufacture. Other minor amounts of material may also be present, such as dopants. Porous silicon 110, 210 has a large surface area of up to 783 $m^2/cm^3$, providing a very large surface for applications such as surface enhanced Raman spectroscopy techniques.

Porous silicon 110, 210 was discovered in the late 1950's by electropolishing silicon in dilute hydrofluoric acid solutions. As is known in the art, porous silicon 110, 210 may be produced by etching a silicon substrate with dilute hydrofluoric acid (HF) in an electrochemical cell. In certain cases, silicon may be initially etched in HF at low current densities. After the initial pores are formed, the silicon may be removed from the electrochemical cell and etched in very dilute HF to widen the pores formed in the electrochemical cell. The composition of the porous silicon substrate 110, 210 will also affect pore size, depending on whether or not the silicon is doped, the type of dopant and the degree of doping. The effect of doping on silicon pore size is known in the art. For embodiments of the invention involving detection and/or identification of large biomolecules, a pore size of about 2 nm to 100 or 200 nm may be selected. The orientation of pores in porous silicon 110, 210 may also be selected in particular embodiments of the invention. For example, an etched 1,0,0 crystal structure will have pores oriented perpendicular to the crystals, while 1,1,1 or 1,1,0 crystal structures will have pores oriented diagonally along the crystal axis. The effect of crystal structure on pore orientation is also known in the art. Crystal composition and porosity may also be regulated to change the optical properties of the porous silicon 110, 210. Such properties may be changed, for example, to enhance Raman signals and decrease background noise and/or to optimize the characteristics of light emitting diodes or field emission electron sources incorporating metal-coated porous silicon 110, 210. The optical properties of porous silicon 110, 210 are known in the art (e.g. Cullis et al., J. Appl. Phys. 82:909-965, 1997; Collins et al, Physics Today 50:24-31, 1997).

In a non-limiting example of a method for producing a porous silicon substrate 110, 210, a silicon wafer may be placed inside an electrochemical cell comprising an inert material, such as Teflon®. The wafer is connected to the positive pole of a constant current source, forming the anode of the electrochemical cell. The negative pole of the constant current source is connected to a cathode, such as a platinum electrode. The electrochemical cell may be filled with a dilute electrolyte solution of HP in ethanol. Alternatively, HF may be dissolved in other alcohols and/or surfactants known in the art, such aspentane or hexane. In certain embodiments of the invention, a computer may be operably coupled to a constant current source to regulate the current, voltage and/or time of electrochemical etching. The silicon wafer exposed to HF electrolyte in the electrochemical cell becomes etched to form a porous silicon substrate 110, 210. As is known in the art, the thickness of the porous silicon layer 110, 210 and the degree of porosity of the silicon may be controlled by regulating the time and/or current density of anodization and the concentration of HF in the electrolyte solution (e.g., U.S. Pat. No. 6,358,815).

In various embodiments of the invention, portions of the silicon wafer may be protected from HF etching by coaling with any known resist compound, such as polymethyl-methacrylate. Lithography methods, such as photolithography, of use for exposing selected portions of a silicon wafer to HF etching are well known in the art. Selective etching may be of use to control the size and shape of a porous Si chamber 110, 210 to be used for Raman spectroscopy or for various electrical devices. In certain embodiments of the invention, a porous silicon chamber 110, 210 of about 1 μm (micrometer) in diameter may be used. In other embodiments of the invention, a trench or channel of porous silicon 110, 210 of about 1 μm in width may be used. The size of the porous silicon chamber 110, 210 is not limiting, and it is contemplated that any size or shape of porous silicon chamber 110, 210 may be used. A 1 μm chamber size may be of use, for example, with an excitatory laser 410 that emits a light beam of about 1 μm in size.

The exemplary method above is not limiting for producing porous silicon substrates 110, 210 and it is contemplated that any method known in the art may be used. Non-limiting examples of methods for making porous silicon substrates 110, 210 include anodic etching of silicon wafers and depositing a silicon/oxygen containing material followed by controlled annealing (e.g., Canham, "Silicon quantum wire array fabrication by electrochemical and chemical dissolution of wafers," Appl. Phys. Lett. 57:1046, 1990; U.S. Pat. Nos. 5,561,304; 6,153,489; 6,171,945; 6,322,895; 6,358,613; 6,358,815; 6,359,276). In various embodiments of the invention, the porous silicon layer 110, 210 may be attached to one or more supporting layers, such as bulk silicon, quartz, glass and/or plastic. In certain embodiments, an etch stop layer, such as silicon nitride, may be used to control the depth of etching. The porous silicon layer 110, 210 may be incorporated into a semiconductor chip, using known methods of chip manufacture. In certain embodiments of the invention, a metal-coated porous silicon 110, 210 chamber may be designed as part of an integral chip, connected to various channels, microchannels, nanochannels, microfluidic channels, reaction chambers, solvent reservoirs 220, waste reservoirs 230, etc. In alternative embodiments, a metal-coated porous silicon 110, 210 chamber may be cut out of a silicon wafer and incorporated into a chip and/or other device.

In certain alternative embodiments of the invention, it is contemplated mat additional modifications to the porous silicon substrate 110, 210 may be made, either before or after metal 150 coating. For example, after etching a porous silicon substrate 110, 210 may be oxidized, using methods known in the art, to silicon oxide and/or silicon dioxide 120.

Oxidation may be used, for example, to increase the mechanical strength and stability of the porous silicon substrate 110, 210 and/or to prevent spontaneous immersion plating of porous silicon 110, 210, which can lead to pore blockage of nanoscale channels. Alternatively, the metal-coated porous silicon substrate 110, 210 may be subjected to further etching to remove the silicon material, leaving a metal 150 shell that may be left hollow or may be filled with other materials, such as one or more additional metals 150.

Metal Coating of Porous Substrates

Porous substrates 110, 210, such as porous silicon 110, 210, may be coated with a metal 150, such as a Raman active metal 150. Exemplary Raman active metals 150 include, but are not limited to gold, silver, platinum, copper and aluminum. Known methods of metal 150 coating include electroplating; cathodic electromigration; evaporation and sputtering of metals 150; using seed crystals to catalyze (i.e. using a copper/nickel seed to plate gold); ion implantation; diffusion; or any other method known in the art for plating thin metal layers 150 on porous substrates 110, 210. (See, e.g., Lopez and Fauchet, "Erbium emission from porous silicon one-dimensional photonic band gap structures," Appl. Phys. Lett. 77:3704-6, 2000; U.S. Pat. Nos. 5,561,304; 6,171,945; 6,359,276.) Another non-limiting example of metal 150 coating comprises electroless plating (e.g., Gole et al., "Patterned metallization of porous silicon from electroless solution for direct electrical contact," J. Electrochem. Soc. 147:3785, 2000). The composition and/or thickness of the metal layer 150 may be controlled to optimize optical and/or electrical characteristics of the metal-coated porous substrates 110, 210.

Arsenic-anodized porous silicon 110, 210 is known to function as a moderate reducing agent for metal ions, thereby initiating spontaneous immersion plating of metal 150 on the top surface of the porous area 110, 210 and closing the pore openings. Thus, using standard methods of metal 150 impregnation, it is difficult to obtain a uniform metal 150 depth profile while maintaining an open porous surface 110, 210. There is a trade-off between the unblocked pores and metal 150 penetration depth, which can be explained as follows. High concentrations of metal ion are needed to obtain a better metal 150 depth profile. However, exposure to high concentrations of metal salt solutions 130 close the pores due to the thick metal film 150 deposition from the spontaneous immersion plating reaction. To maintain an open pore, the concentration of metal ion in solution 130 needs to be lower. However, this causes poorer penetration depth, as well as reducing the amount of metal 150 deposited. This problem is resolved by the methods disclosed herein, which allow a more uniform metal 150 deposition without pore clogging.

Metal Coating by Thermal Decomposition of a Metal Salt

As illustrated in FIG. 1, in particular embodiments of the invention a porous silicon substrate 110 may be uniformly coated with a metal 150, such as a Raman sensitive metal 150, by a method comprising thermal decomposition of a metal salt layer 140. In particular embodiments of the invention, the metal 150 is silver. A porous silicon substrate 110 (FIG. 1A) may be obtained, for example, as disclosed above. To prevent premature metal 150 deposition and pore blocking, the surface layer of silicon may be oxidized to silicon dioxide 120 (FIG. 1B), for example by chemical oxidation or plasma oxidation. Oxidation prevents spontaneous immersion plating by stabilizing the porous silicon 110 surface. In the absence of oxidation, positively charged silver cations can engage in a redox reaction with unoxidized silicon, resulting in spontaneous silver metal 150 deposition.

Figure 1A:
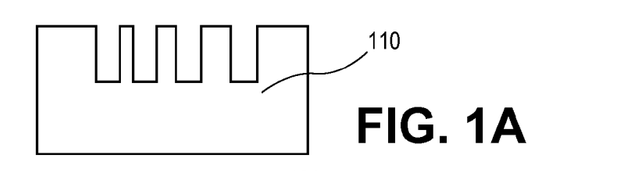
FIG. 1A shows a porous silicon substrate 110.
Figure 1B:
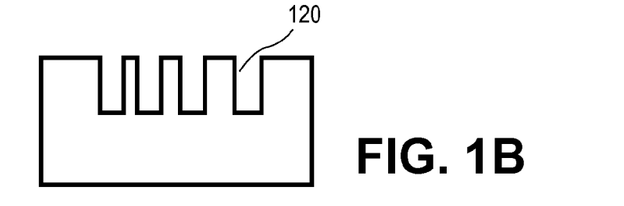
FIG. 1B illustrates silicon oxidation, for example by plasma oxidation, to form a layer of silicon dioxide 120.
Figure 1C:
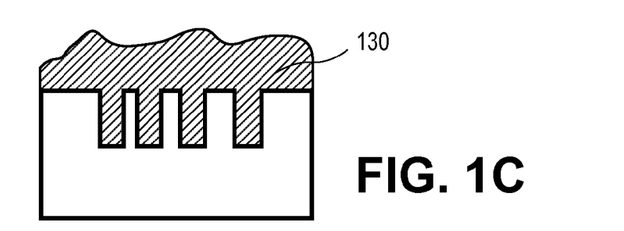
FIG. 1C shows immersion of the oxidized porous silicon 110 in a metal salt solution 130, such as a silver nitrate solution 130.
Figure 1D:
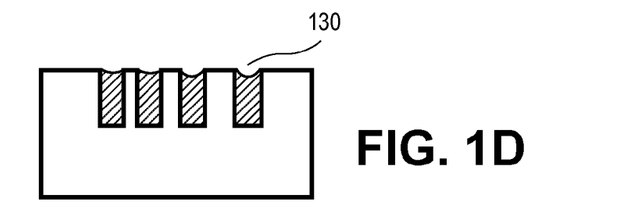
FIG. 1D illustrates removal of excess metal salt solution 130.
Figure 1E:
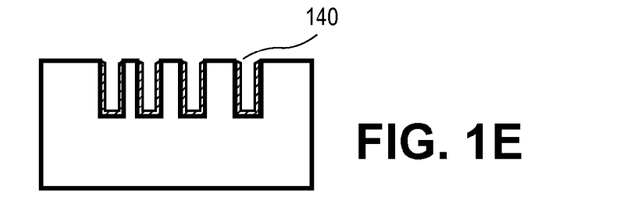
FIG. 1E shows drying of the solution 130 to form a thin layer of dry metal salt 140 on the porous silicon substrate 110.
Figure 1F:
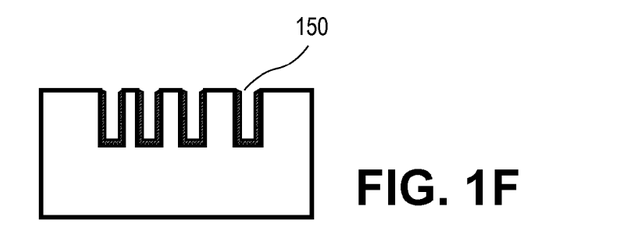
FIG. 1F illustrates thermal decomposition of the dry metal salt 140 to form a uniform layer of metal 150 coating the porous silicon substrate 110.

Following oxidation, the porous silicon substrate 110 is wet with a metal salt solution 130, such as a 1 M solution of silver nitrate (AgNOs) (FIG. 1C). In a non-limiting example, the oxidized porous silicon substrate 110 is dipped into a silver nitrate solution 130 for 20 minutes, until the pores are completely wet with the silver nitrate solution 130. Excess metal salt solution 130 is removed, for example, by nitrogen gun drying (FIG. 1D). The solution 130 remaining in the pores may be dried, for example, by heating to 100° C. for 20 min. At this point, the solvent has evaporated and a thin layer of dry silver nitrate salt 140 is deposited on the surface of the porous silicon 110. The dry salt 140 may be thermally decomposed (FIG. 1F), for example by heating to 500° C. for 30 min in an ambient pressure furnace. The reaction of Equation 1 occurs spontaneously at temperatures above 573° K. (about 300° C.). The nitrate ion is converted to gaseous nitrogen dioxide according to Equation 1, resulting in deposition of a uniform layer of metallic silver 150 coating the porous silicon substrate 110 (FIG. 1F). Although nitrogen dioxide has been used as a photoetching agent, under the conditions of the disclosed method it does not appear to etch the silicon dioxide layer 120.

$$AgNO_3 \rightarrow Ag(s) + NO_2(gas) + \frac{1}{2}O_2(gas) \qquad (1)$$

The thickness of the deposited metal layer 150 may be controlled, for example, by varying the concentration of the metal salt solution 130. Depending on the thickness of metal layer 150 to be deposited, the salt solution 130 concentration can vary between a wide range, of about 0.1, 0.2, 0.3, 0.4, 0.5, 0.6, 0.7, 0.8, 0.9, 1.0, 1.25, 1.5, 1.75, 2.0, 2.5, 3.0, 3.5, 4.0, 4.5 to 5.0 M (molar), Although the exemplary method utilizes a silver solution 130, the embodiments of the invention are not limited to depositing silver 150 but may encompass any known metal 150, including but not limited to Raman active metals 150 such as gold, copper, platinum, aluminum, etc. The methods are also not limited as to the type of salt used. In certain embodiments of the invention, the anionic species used to form the metal salt may be one that is converted to a gaseous species and driven off during the thermal decomposition process, such as nitrate or sulfate ion. However, in alternative embodiments any anionic species without limitation may be used.

Metal Coating by Microfluidic Impregnation

Figure 2:
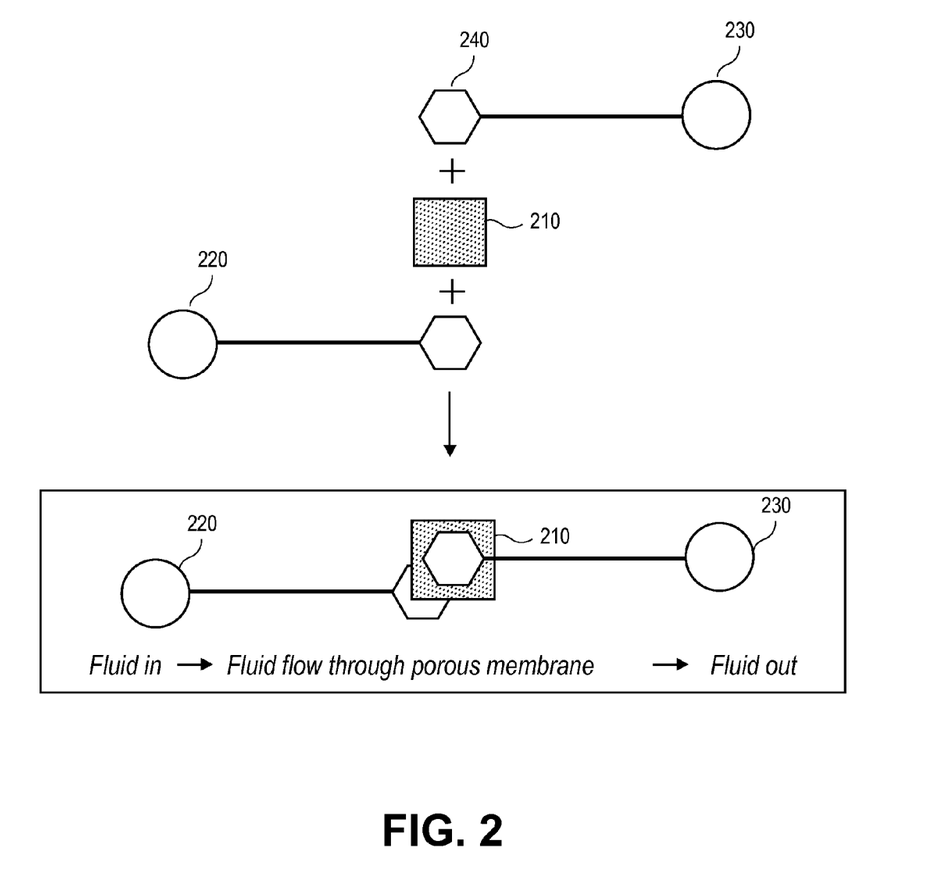
FIG. 2 illustrates another exemplary method for producing a metal-coated porous silicon substrate 210 comprising microfluidic impregnation.

In alternative embodiments of the invention illustrated in FIG. 2, a porous membrane 210, such as a porous silicon membrane 210, may be coated with metal 150 using microfluidic impregnation. In an exemplary method, a porous silicon membrane 210 may be obtained as disclosed above. The porous silicon layer 210 may be electropolished and suspended in a solution. The electropolished membrane 210 may be inserted into a microfluidic pathway between one or more solvent reservoirs 220 and a waste reservoir 230 that are connected through cross-paths 240. Such microfluidic pathways may be produced by any method known in the art, such as micromolding with PDMS (polydimethyl siloxane), standard lithography techniques or photolithography and etching of various chip materials (e.g., Duffy et al., *Anal. Chem.* 70:4974-84, 1998). The porous silicon membrane 210 may be incorporated into any type of microfluidic system. In certain embodiments of the invention, microfluidic systems incorporating porous silicon membranes 210 may be of use for a wide variety of applications relating to analysis and/or separation of polymer molecules, including but not limited to proteins and nucleic acids. Methods for micro and/or nanoscale manufacturing are known in the art, as discussed in more detail below.

A metal salt solution 130, such as a silver nitrate solution 130, may be introduced through the solvent reservoir 220 and allowed to flow through the porous silicon membrane 210 to a waste reservoir 230. A spontaneous reaction will occur, as indicated in Equation 2.

$$Ag^+(aq.) + Si(surface) + 2H_2O(liquid) \rightarrow Ag(solid) + H_2(gas) + SiO_2(surface) + 2H^+ \quad (2)$$

As disclosed in Equation 2, an aqueous metal solution 130 reacts spontaneously with a porous silicon surface 210 in a redox reaction, producing a deposited metal 150 coating on the porous silicon 210. The thickness of the metal 150 coating may be controlled by the metal salt concentration of the solution 130, the rate of flow through the microfluidic pathway, the temperature, and/or the length of time that the solution 130 is allowed to flow through the membrane 210. Techniques for controlling such metal 150 plating reactions are known in the art.

Figure 3:
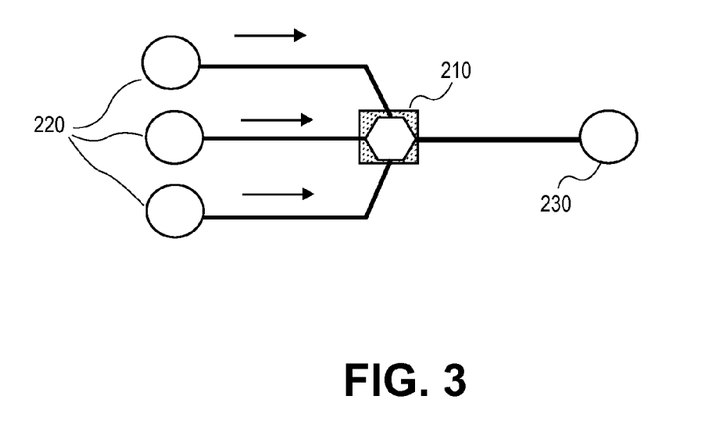
FIG. 3 illustrates an alternative embodiment of the invention for delivering different metal plating solutions to a porous silicon substrate 210.

The method is not limited to silver solutions 130, but may also be performed with solutions 130 of other metal salts, including but not limited to Raman active metals 150 such as gold, platinum, aluminum, copper, etc. In other alternative embodiments of the invention, the porous silicon membrane 210 may be coated with two or more different metals 150, using multiple solvent reservoirs 220 containing different metal plating solutions 130 (FIG. 3). In certain embodiments of the invention, one or more reservoirs 220 may contain a wash solution to remove excess metal plating solution 130. Coating with multiple metals 150 may be used to manipulate the electrical, optical and/or Raman surface characteristics of the metal-coated porous silicon membrane 210, such as the degree of surface enhancement of the Raman signal, the distance from the surface 210 at which resonance occurs, the range of wavelengths of Raman resonance, etc.

The disclosed methods result in the production of a metal-coated porous silicon membrane 210 integrated into a microfluidic pathway. Such an integrated microchip may be directly incorporated into a Raman detection system 400 as exemplified in FIG. 4. One or more samples suspected of containing target molecules may be loaded into corresponding solvent reservoirs 220. Samples may be channeled through the microfluidic pathway to enter the metal-coated membrane 210. Once in the membrane 210, the target molecule may be excited by an excitatory light source 410, such as a laser 410. An emitted Raman signal may be detected by a Raman detector 420, as discussed in more detail below. Once analyzed, samples may be removed into a waste reservoir 230, the membrane 210 washed and the next sample analyzed. The Raman detection system 400 may incorporate various components known in the art, such as Raman detectors 420 and excitatory light sources 410, or may comprise custom components designed to be fully integrated into the system 400 to optimize Raman detection of analytes.

Micro-Electro-Mechanical Systems (MEMS)

In some embodiments of the invention, a metal-coated porous silicon substrate 110, 210 may be incorporated into a larger apparatus and/or system 400. In certain embodiments, the substrate 110, 210 may be incorporated into a micro-electro-mechanical system (MEMS) 400. MEMS are integrated systems 400 comprising mechanical elements, sensors, actuators, and electronics. All of those components may be manufactured by known microfabrication techniques on a common chip, comprising a silicon-based or equivalent substrate (e.g., Voldman et al, *Ann. Rev. Biomed. Eng.* 1:401-425, 1999). The sensor components of MEMS may be used to measure mechanical, thermal, biological, chemical, optical and/or magnetic phenomena. The electronics may process the information from the sensors and control actuator components such pumps, valves, heaters, coolers, filters, etc. thereby controlling the function of the MEMS.

The electronic components of MEMS may be fabricated using integrated circuit (IC) processes (e.g., CMOS, Bipolar, or BICMOS processes). They may be patterned using photolithographic and etching methods known for computer chip manufacture. The micromechanical components may be fabricated using compatible "micromachining" processes that selectively etch away parts of the silicon wafer or add new structural layers to form the mechanical and/or electromechanical components.

Basic techniques in MEMS manufacture include depositing thin films of material on a substrate, applying a patterned mask on top of the films by photolithographic imaging or other known lithographic methods, and selectively etching the films. A thin film may have a thickness in the range of a few nanometers to 100 micrometers. Deposition techniques of use may include chemical procedures such as chemical vapor deposition (CVD), electrodeposition, epitaxy and thermal oxidation and physical procedures like physical vapor deposition (PVD) and casting. Methods for manufacture of nanoelectromechanical systems may be used for certain embodiments of the invention. (See, e.g., Craighead, Science 290:1532-36, 2000.)

In some embodiments of the invention, metal-coated porous silicon substrates 110, 210 may be connected to various fluid filled compartments, such as microfluidic channels, nanochannels and/or microchannels. These and other components of the apparatus may be formed as a single unit, for example in the form of a chip as known in semiconductor chips and/or microcapillary or microfluidic chips. Alternatively, the metal-coated porous silicon substrate 110, 210 may be removed from a silicon wafer and attached to other components of an apparatus. Any materials known for use in such chips may be used in the disclosed apparatus, including silicon, silicon dioxide 120, silicon nitride, polydimethyl siloxane (PDMS), polymethylmethacrylate (PMMA), plastic, glass, quartz, etc.

Techniques for batch fabrication of chips are well known in the fields of computer chip manufacture and/or microcapillary chip manufacture. Such chips may be manufactured by any method known in the art, such as by photolithography and etching, laser ablation, injection molding, casting, molecular beam epitaxy, dip-pen nanolithography, chemical vapor deposition (CVD) fabrication, electron beam or focused ion beam technology or imprinting techniques. Non-limiting examples include conventional molding with a flowable, optically clear material such as plastic or glass; photolithography and dry etching of silicon dioxide 120; electron beam lithography using polymethylmethacrylate resist to pattern an aluminum mask on a silicon dioxide 120 substrate, followed by reactive ion etching. Known methods for manufacture of nanoelectromechanical systems may be used for certain embodiments of the invention. (See, e.g., Craighead, Science 290:1532-36, 2000.) Various forms of microfabricated chips are commercially available from, e.g., Caliper Technologies Inc. (Mountain View, Calif.) and ACLARA Biosciences Inc. (Mountain View, Calif.).

In certain embodiments of the invention, part or all of the apparatus may be selected to be transparent to electromagnetic radiation at the excitation and emission frequencies used for Raman spectroscopy, such as glass, silicon, quartz or any other optically clear material. For fluid-filled compartments that may be exposed to various biomolecules, such as proteins, peptides, nucleic acids, nucleotides and the like, the surfaces exposed to such molecules may be modified by coating, for example to transform a surface from a hydrophobic to a hydrophilic surface and/or to decrease adsorption of molecules to a surface. Surface modification of common chip materials such as glass, silicon, quartz and/or PDMS is known in the art (e.g., U.S. Pat. No. 6,263,286). Such modifications may include, but are not limited to, coating with commercially available capillary coatings (Supelco, Bellafonte, Pa.), silanes with various functional groups such as polyethyleneoxide or acrylamide, or any other coating known in the art.

Raman Spectroscopy

In certain embodiments of the invention, the disclosed methods, systems 400 and apparatus are of use for the detection and/or identification of analytes by surface enhanced Raman spectroscopy (SERS), surface enhanced resonance Raman spectroscopy (SERRS) and/or coherent anti-Stokes Raman spectroscopy (CARS) detection. Compared to existing techniques, the disclosed methods, systems 400 and apparatus provide SERS active substrates with increased and more uniform metal 150 density and greater depth of field of SERS enhancement, allowing more efficient Raman detection and/or identification of analytes.

Previous methods for SERS detection of various analytes have used colloidal metal 150 particles, such as aggregated silver 150 nanoparticles, that were typically coated onto a substrate and/or support (e.g., U.S. Pat. Nos. 5,306,403; 6,149,868; 6,174,677; 6,376,177). While such arrangements occasionally allow SERS detection with as much as $10^6$ to $10^8$ increased sensitivity, they are not capable of single molecule detection of small analytes such as nucleotides, as disclosed herein. Enhanced sensitivity of Raman detection is apparently not uniform within a colloidal particle aggregate, but rather depends on the presence of "hot spots." The physical structure of such hot spots, the range of distances from the metal 150 nanoparticles at which enhanced sensitivity occurs, and the spatial relationships between aggregated nanoparticles and analytes that allow enhanced sensitivity have not been characterized. Further, aggregated metal 150 nanoparticles are inherently unstable in solution, with adverse effects on the reproducibility of single molecule detection. The present methods, systems 400 and apparatus provide a stable microenvironment for SERS detection in which the physical conformation and density of the Raman-active metal 150 porous substrate 110, 210 may be precisely controlled, allowing reproducible, sensitive and accurate detection of analytes in solution.

Raman Detectors

In some embodiments of the invention, analytes may be detected and/or identified by any known method of Raman spectroscopy. In such embodiments, the metal-coated porous substrate 110, 210 may be operably coupled to one or more Raman detection units. Various methods for detection of analytes by Raman spectroscopy are known in the art. (See, e.g., U.S. Pat. Nos. 6,002,471; 6,040,191; 6,149,868; 6,174,677; 6,313,914). Variations on surface enhanced Raman spectroscopy (SERS), surface enhanced resonance Raman spectroscopy (SERRS), hyper-Raman spectroscopy and coherent anti-Stokes Raman spectroscopy (CARS) have been disclosed. In SERS and SERRS, the sensitivity of the Raman detection is enhanced by a factor of $10^6$ or more for molecules adsorbed on roughened metal 150 surfaces, such as silver, gold, platinum, copper or aluminum surfaces.

A non-limiting example of a Raman detection unit is disclosed in U.S. Pat. No. 6,002,471. An excitation beam may be generated by either a frequency doubled Nd:YAG laser 410 at 532 nm wavelength or a frequency doubled Ti:sapphire laser 410 at 365 nm wavelength. Alternatively, excitation beams may be generated at 785 nm using a Ti:sapphire laser 410 or 514 nm using an argon laser 410. Pulsed laser beams or continuous laser beams may be used. The excitation beam passes through confocal optics and a microscope objective, and is focused onto the Raman active substrate 110, 210 containing one or more analytes. The Raman emission light from the analytes is collected by the microscope objective and the confocal optics and is coupled to a monochromator for spectral dissociation. The confocal optics includes a combination of dichroic filters, barrier filters, confocal pinholes, lenses, and mirrors for reducing the background signal. Standard full field optics can be used as well as confocal optics. The Raman emission signal is detected by a Raman detector 420, comprising an avalanche photodiode interfaced with a computer for counting and digitization of the signal.

Another example of a Raman detection unit is disclosed in U.S. Pat. No. 5,306,403, including a Spex Model 1403 double-grating spectrophotometer with a gallium-arsenide photomultiplier tube (RCA Model C31034 or Burle Industries Model C3103402) operated in the single-photon counting mode. The excitation source comprises a 514.5 nm line argon-ion laser 410 from SpectraPhysics, Model 166, and a 647.1 nm line of a krypton-ion laser 410 (Innova 70, Coherent).

Alternative excitation sources include a nitrogen laser 410 (Laser Science Inc.) at 337 nm and a helium-cadmium laser 410 (Liconox) at 325 nm (U.S. Pat. No. 6,174,677), a light emitting diode 410, an Nd:YLF laser 410, and/or various ion lasers 410 and/or dye lasers 410. The excitation beam may be spectrally purified with a bandpass filter (CHROMA) and may be focused on the Raman active substrate 110, 210 using a 20× objective lens (Nikon). The objective lens may be used to both excite the analytes and to collect the Raman signal, by using a holographic beam splitter (Kaiser Optical Systems, Inc., Model HB 647-26N18) to produce a right-angle geometry for the excitation beam and the emitted Raman signal. A holographic notch filter (Kaiser Optical Systems, Inc.) may be used to reduce Rayleigh scattered radiation. Alternative Raman detectors 420 include an ISA HR-320 spectrograph equipped with a red-enhanced intensified charge-coupled device (RE-ICCD) detection system (Princeton Instruments). Other types of detectors 420 may be used, such as Fourier-transform spectrographs (based on Michaelson interferometers), charged injection devices, photodiode arrays, InGaAs detectors, electron-multiplied CCD, intensified CCD and/or phototransistor arrays.

Any suitable form or configuration of Raman spectroscopy or related techniques known in the art may be used for detection of analytes, including but not limited to normal Raman scattering, resonance Raman scattering, surface enhanced Raman scattering, surface enhanced resonance Raman scattering, coherent anti-Stokes Raman spectroscopy (CARS).

EXAMPLES

Example 1

Construction of a Porous Silicon Substrate

Formation of Porous Nanocrystalline Silicon

Methods for making nanocrystalline porous silicon 110, 210 are known in the art (e.g., U.S. Pat. No. 6,017,773). A layer of nanocrystalline porous silicon 110, 210 may be formed electrochemically as disclosed in Petrova-Koch et al. (Appl. Phys. Let. 61:943, 1992). Depending on the particular application, the silicon may be lightly or heavily p-doped or n-doped prior to etching to regulate the characteristics of the porous silicon substrate 110, 210. Single crystal silicon ingots may be grown by the well known Czochralski method (e.g., http://www.msil.ab.psiweb.com/engiish/msilhist4-e.html). A single crystal silicon wafer may be treated with anodic etching in dilute HF/electrolyte to form a nanocrystalline porous silicon substrate 110, 210. Alternatively, chemical etching in a solution of HF, nitric acid and water may be used without anodic etching. Ethanol may be used as a wetting agent to improve pore wetting with the HF solution.

The wafer may be coated with polymethyl-methacrylate resist or any other known resist compound before etching. A pattern for the nanocrystalline porous silicon substrate 110, 210 may be formed by standard photolithographic techniques. In different embodiments of the invention, the nanocrystalline porous substrate 110, 210 may be circular, trench shaped, channel shaped or of any other selected shape. In certain embodiments, multiple porous substrates 110, 210 may be formed on a single silicon wafer to allow for multiple sampling channels and/or chambers for Raman analysis. Each sampling channel and/or chamber may be operably coupled to one or more Raman detectors 420.

After resist coating and lithography, the wafer may be exposed to a solution of between about 15 to 50 weight percent HF in ethanol and/or distilled water in an electrochemical cell comprised of Teflon®. Etching may be performed in the dark (p-type silicon) or in the light (n-type or p-type silicon). In different embodiments of the invention, the entire resist coated wafer may be immersed in an HF solution. In alternative embodiments, the wafer may be held in place in the electrochemical cell, for example using a synthetic rubber washer, with only a portion of the wafer surface exposed to the HF solution (U.S. Pat. No. 6,322,895). In either case, the wafer may be electrically connected to the positive pole of a constant current source to form the anode of the electrochemical cell. A platinum electrode may provide the cathode for the cell. The wafer may be etched using an anodization current density of between 5 to 250 milliamperes/$cm_2$ for between 5 seconds to 30 minutes in the dark; depending on the selected degree of porosity. In particular embodiments of the invention, a porosity of about 10%, 15%, 20%, 25%, 30%, 35%, 40%, 45%, 50%, 60%, 70%, 80% or 90% may be selected. As is known in the art, the anodization current density required to form porous silicon 110, 210 may depend in part on the type of silicon substrate used, such as whether the substrate is lightly or heavily p-type (boron doped) or n-type (phosphorus doped).

In other alternative embodiments of the invention, the nanocrystalline porous silicon substrate 110, 210 may be incorporated into a MEMS device comprising a variety of detectors 420, sensors, electrodes, other electrical components, mechanical actuators, etc. using known chip manufacturing techniques. In certain embodiments, such manufacturing procedures may occur before and/or after, formation of the porous silicon substrate 110, 210 and/or coating with a Raman sensitive metal 150.

Example 2

Metal Coating of Porous Silicon by Thermal Decomposition

FIG. 1 illustrates an exemplary method for uniformly impregnating metal 150 into nanoporous silicon 110. The surface of the porous silicon 110 is oxidized to silicon dioxide 120 (FIG. 1B). A metal salt solution 130 is diffused into the porous matrix 110 (FIG. 1C) and dried (FIG. 1E). The dried metal salt 140 is thermally decomposed inside the pores to form a uniform metal layer 150 (FIG. 1F). Oxidation of the porous silicon surface 110 enables complete wetting of porous silicon 110 in the metal salt solution 130, while preventing spontaneous immersion coating, which causes pore blockage. The dry metal salt 140 is thermally decomposed in a furnace and pure metal 150 is deposited on the side walls of the nanopores. A uniform, thin metal 150 coating of nanoporous silicon 110 may be obtained without plugging the pores, as often observed with standard methods of metal 150 infiltration into nanoporous silicon 110. Currently available plating methods are also diffusion limited, resulting in non-uniform metal 150 deposition that can decrease the reproducibility of analyte detection, depending upon where in the metal-coated substrate 110 the analyte is located.

An optimal immersion time and high metal ion concentration are needed to make the metal 150 coat the entire porous structure 110. These requirements can be satisfied by oxidizing the surface of porous silicon 110, either by chemical oxidation or plasma oxidation, prior to exposure to a metal salt solution 130 (FIG. 1B). Oxidation prevents spontaneous immersion plating by stabilizing the porous surface 110. The oxidized porous silicon 110 may thus be immersed in highly concentrated metal salt solution 130 without causing pore blockage (FIG. 1C). Excessive metal salt solution 130 may be removed, for example by blowing nitrogen gas (FIG. 1D). The solvent is evaporated to increase absorption of metal salt 140 on the porous surface 110 (FIG. 1E). The metal salts 140 are thermally decomposed (FIG. 1F) to form a uniform deposit of Raman active metal 150 on the surface of the porous silicon substrate 110.

In a non-limiting example a porous silicon substrate 110 was formed by electrochemical etching in a 15% HF solution, exposing boron doped crystalline silicon to a current density of 50 mA/$cm^2$. The porous silicon substrate 110 was subjected to plasma oxidation in a Technics oxygen plasma chamber at an oxygen flow rate of 50 seem (standard cubic centimeters) and radiofrequency power of 300 W (watts) for 20 min, resulting in formation of an approximately 50 Å (Angstrom) silicon dioxide 120 layer on the surface of the pores. Alternatively, chemical oxidation in piranha solution may be used (e.g., http://www-device.eecs.Berkeley.edu/~daewon/labweek7.pdf). The silicon dioxide 120 layer passivates the silicon dangling bond, preventing fast immersion coating.

The oxidized porous silicon 110 was dipped in a 1 M $AgNO_3$ solution 130 for 20 min at room temperature to completely wet the pores with silver nitrate solution 130. Excessive silver nitrate solution 130 was removed by nitrogen gun drying to prevent pore closure by excessive silver 150 deposition. The solvent was removed from the remaining silver nitrate solution 130 by drying at 100° C. for 20 min. At this stage all the solvent was evaporated and dry silver nitrate salt 140 was absorbed on the surface of pores, resulting in an observable brown color on the surface of the porous silicon 110.

Figure 5A:
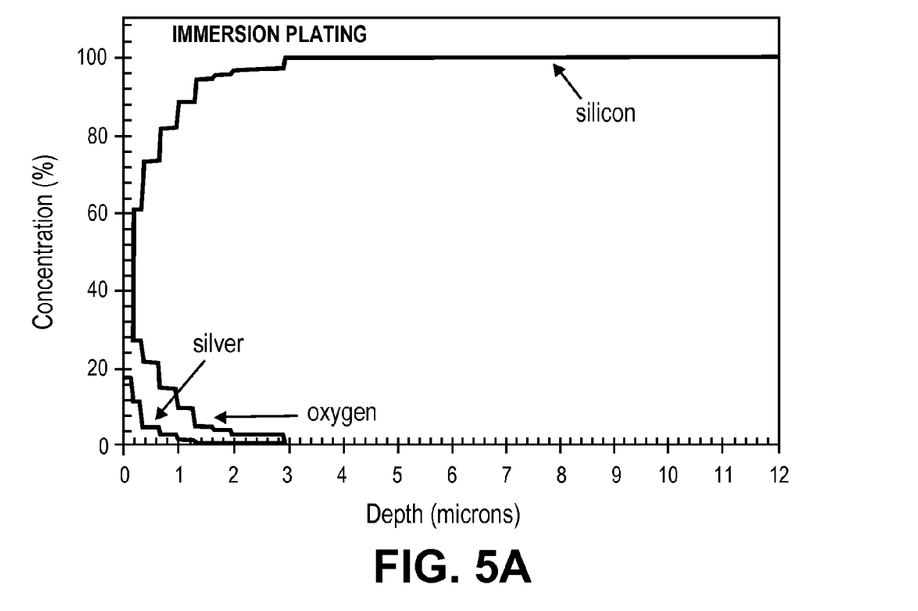
FIG. 5 illustrates the uniform deposition of an exemplary metal 150 (silver) on a porous silicon substrate 110 using a thermal decomposition method.
Figure 5B:
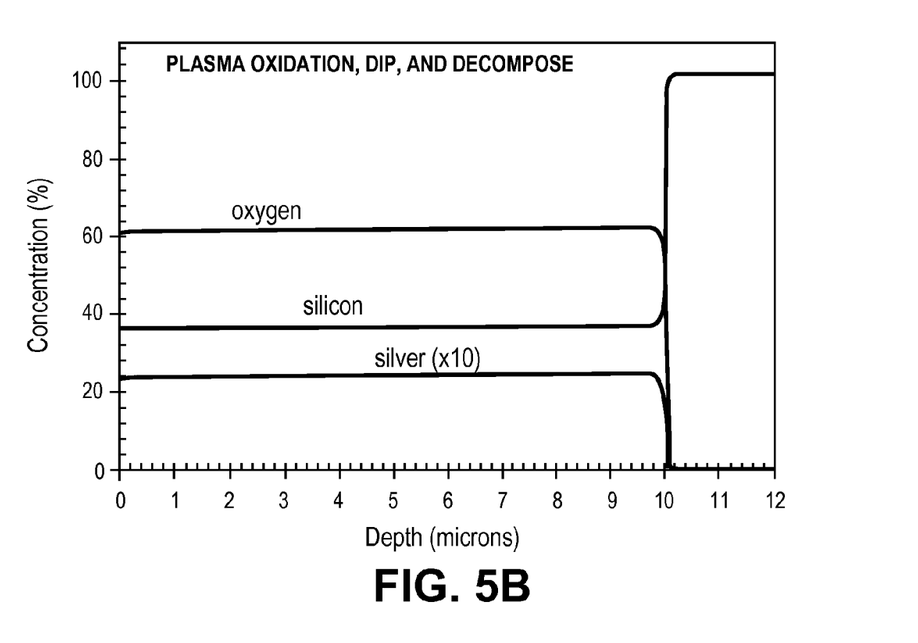

Thermal decomposition was performed for 30 min at 500° C. in an ambient pressure furnace, resulting in the decomposition of the dry silver nitrate salt 140 to silver metal 150. The method disclosed herein resulted in the formation of a highly uniform deposit of silver metal 150 on the surface of the porous silicon substrate 110, as shown in FIG. 5. FIG. 5 illustrates the silver depth profile obtained on nanoporous silicon 110, as determined by Rutherford backscattering spectroscopy analysis. The silver depth profile was compared for nanoporous silicon 110 treated by conventional diffusion limited immersion plating in a 1 mM AgNO$_3$ solution 130 for 2.5 min (FIG. 5A) versus the method of the present Example (FIG. 5B). As can be seen, the present method resulted in a highly uniform silver 150 deposit, of much greater penetration depth compared to the standard method (FIG. 5A and FIG. 5B). The present method resulted in a uniform silver 150 deposit up to about 10 μm in depth (FIG. 5B), while the standard method resulted in a highly non-uniform deposit of less than 3 μm in depth (FIG. 5A). The Rutherford backscattering data were corrected using scanning electron microscopy analysis to determine the actual thickness of the porous silicon 110 layer.

Comparing the distribution of silver 150 versus silicon using the present method (FIG. 5B), it is observed that the silver 150 deposition is uniform down to the level at which the silicon density reaches a maximum. That is, the data of FIG. 5B indicate that the metal deposit 150 obtained with the present method extends homogeneously all the way to the bottom of the pores in the porous silicon substrate 110. It is clear that using the standard method (FIG. 5A) the metal deposit 150 ends well before the bottom of the pores.

Example 3

Raman Detection of Analytes

Figure 4:
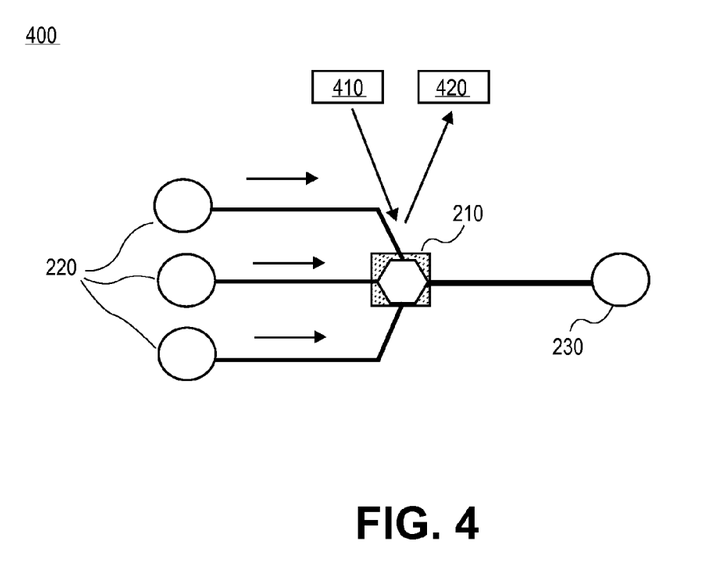
FIG. 4 shows an exemplary system 400 for detecting various target molecules using a metal-coated porous silicon substrate 210 and Raman detection.

A Raman active metal-coated substrate 110, 210 formed as disclosed above may be incorporated into a system 400 for Raman detection, identification and/or quantification of analytes, as exemplified in FIG. 4. The substrate 110, 210 may be incorporated into, for example, a flow through cell, connected via inlet and outlet channels to one or more solvent reservoirs 220 and a waste reservoir 230. Alternatively, the inlet channel may be connected to one or more other devices, such as a sample injector and/or reaction chamber. Analytes may enter the flow through cell and pass across the Raman active substrate 110, 210, where they may be detected by a Raman detection unit. The detection unit may comprise a Raman detector 420 and a light source 410, such as a laser. The laser 410 may emit an excitation beam, activating the analytes and resulting in emission of Raman signals. The Raman signals are detected by the detector 420. In certain embodiments of the invention, the detector 420 may be operably coupled to a computer that can process, analyze, store and/or transmit data on analytes present in the sample.

In an exemplary embodiment of the invention, the excitation beam is generated by a titanium:sapphire laser 410 (Tsunami by Spectra-Physics) at a near-infrared wavelength (750~950 nm) or a galium aluminum arsenide diode laser 410 (PI-ECL series by Process Instruments) at 785 nm or 830 nm. Pulsed laser beams or continuous beams may be used. The excitation beam is reflected by a dichroic mirror (holographic notch filter by Kaiser Optical or an interference filter by Chroma or Omega Optical) into a collinear geometry with the collected beam. The reflected beam passes through a microscope objective (Nikon LU series), and is focused onto the Raman active substrate 110, 210 where target analytes are located. The Raman scattered light from the analytes is collected by the same microscope objective, and passes the dichroic mirror to the Raman detector 420. The Raman detector 420 comprises a focusing lens, a spectrograph, and an array detector. The focusing lens focuses the Raman scattered light through the entrance slit of the spectrograph. The spectrograph (RoperScientific) comprises a grating that disperses the light by its wavelength. The dispersed light is imaged onto an array detector (back-illuminated deep-depletion CCD camera by RoperScientific). The array detector is connected to a controller circuit, which is connected to a computer for data transfer and control of the detector function.

In various embodiments of the invention, the detection unit is capable of detecting, identifying and/or quantifying a wide variety of analytes with high sensitivity, down to single molecule detection and/or identification. In certain embodiments of the invention, the analytes may comprise single nucleotides that may or may not be Raman labeled. In other embodiments, one or more oligonucleotide probes may or may not be labeled with distinguishable Raman labels and allowed to hybridize to target nucleic acids in a sample. The presence of a target nucleic acid may be indicated by hybridization with a complementary oligonucleotide probe and Raman detection using the system 400 of FIG. 4. Alternatively, amino acids, peptides and/or proteins of interest may be detected and/or identified using the disclosed methods and apparatus. The skilled artisan will realize that the methods and apparatus are not limiting as to the type of analytes that may be detected, identified and/or quantified, but rather that any analyte, whether labeled or unlabeled, that can be detected by Raman detection may be analyzed within the scope of the claimed subject matter.

Example 4

Detection of Rhodamine 6G (R6G) by SERS

Figure 6:
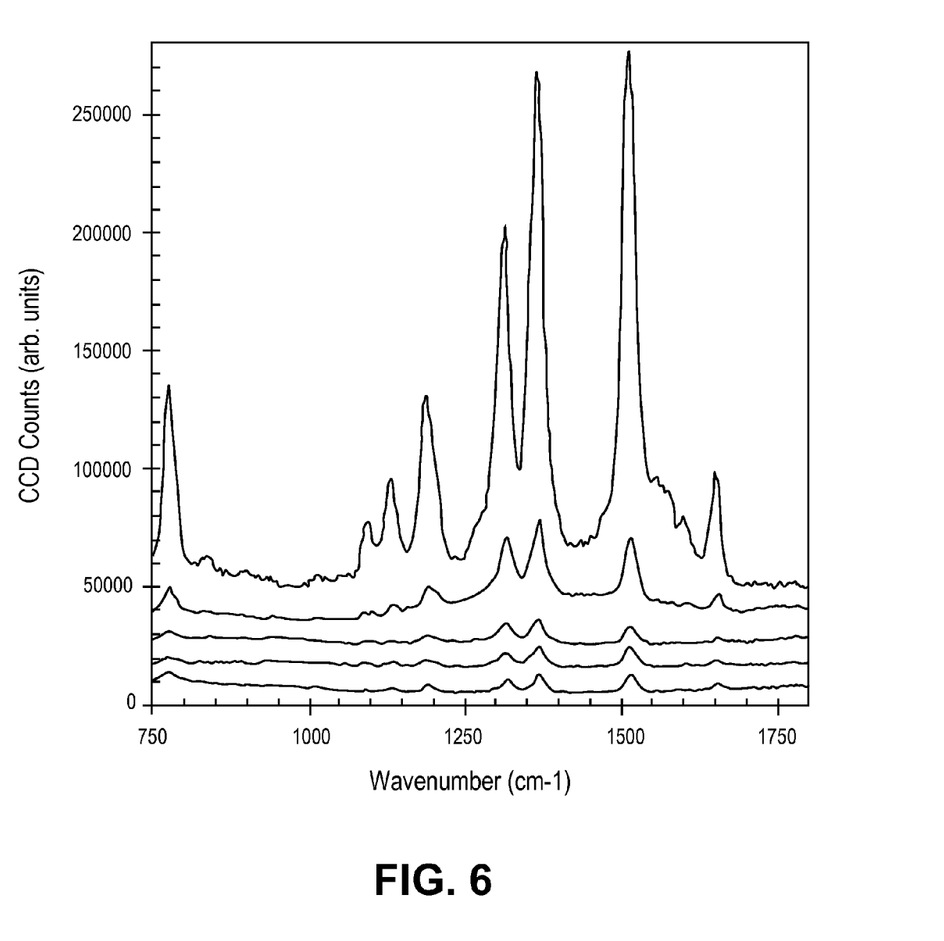
FIG. 6 shows the surface-enhanced Raman spectrum for an exemplary analyte, rhodamine 6G (R6G) dye molecules, obtained with a plasma-oxidized, dip and decomposed (PODD) porous silicon substrate 110 uniformly coated with silver 150. The PODD substrate 110 was prepared by the method of FIG. 1. A solution of 114 nM (micromolar) R6G molecules was subjected to SERS (surface enhanced Raman spectroscopy) using excitation at 785 nm (nanometers).

FIG. 6 illustrates the use of the disclosed methods, systems 400 and apparatus for detection and identification of an exemplary analyte, rhodamine 6G (R6G) dye molecules. R6G is a well-characterized dye molecule that may be obtained from standard commercial sources, such as Molecular Probes (Eugene, Oreg.). A 114 μM (micromolar) solution of R6G was prepared and analyzed by surface enhanced Raman spectroscopy (SERS), using a plasma-oxidized, dip and decomposed (PODD) silver-coated porous silicon substrate 110 that was prepared by the method of Examples 1 and 2. Porous silicon substrates 110 of varying degrees of average porosity were prepared by varying the etching conditions. The R6G solution was diffused into the PODD silver-coated substrate 110 and analyzed by SERS, according to the method of Example 3, using an excitation wavelength of 785 ran. A chemical enhancer (lithium chloride or sodium bromide, about 1 μM concentration) was added to enhance the Raman signal.

The resulting SERS emission spectra, obtained in PODD silver-coated porous substrates 110 of varying porosity, are shown in FIG. 6. FIG. 6 shows SERS emission spectra for 114 μM R6G obtained at average porosities, in order from the lowest trace to the highest trace, of 52%, 55%, 65%, 70% and 77%. As indicated in FIG. 6, the intensity of the SERS emission peaks increases with increasing average porosity in this range, with a highest intensity observed at 77% average porosity. Increasing the porosity above 77% pushes the porous silicon layer 110 into a non-stable materials regime, which can result in physical separation of the porous layer 110 from the bulk silicon substrate. At 77% porosity, scanning electron micrographs showed pore diameters of about 32 nm in width (not shown).

At 77% average porosity, a seven order of magnitude ($10^7$) increase in intensity of the Raman emission spectrum was observed. This compares with an approximately six order of magnitude enhancement observed on a roughened silver 150 plate (not shown). Although the intensity of the SERS emission peaks increased as a function of average porosity, the wavelengths of the emission peaks did not vary (FIG. 6), allowing the identification of R6G independent of the average porosity used. With an estimated detection volume of $1.25 \times 10^{-16}$ liters, the corresponding number of molecules of rhodamine 6G detected was approximately 9 molecules, Additional studies were performed with a solution of adenine, which is a more biologically relevant target molecule. Unique spectroscopic features were detected from a 90 solution of adenine on a porous silicon substrate 110 coated with silver 150.

All of the METHODS, SYSTEMS 400 and APPARATUS disclosed and claimed herein can be made and used without undue experimentation in light of the present disclosure. It will be apparent to those of skill in the art that variations may be applied to the METHODS, SYSTEMS 400 and APPARATUS described herein without departing from the concept, spirit and scope of the claimed subject matter. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the claimed subject matter.

All of the METHODS, SYSTEMS 400 and APPARATUS disclosed and claimed herein can be made and used without undue experimentation in light of the present disclosure. It will be apparent to those of skill in the art that variations may be applied to the METHODS, SYSTEMS 400 and APPARATUS described herein without departing from the concept, spirit and scope of the claimed subject matter. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the claimed subject matter.

What is claimed is:

1. A microfluidic system comprising a porous silicon substrate wherein the porous silicon substrate has a metal coating, a microfluidic pathway wherein the microfluidic pathway is operably coupled to the porous silicon substrate wherein the microfluidic pathway is capable of allowing a fluid to be delivered to the porous silicon substrate, and a detection system capable of detecting a change in a region of the porous silicon substrate comprising the metal coating.

2. The microfluidic system of claim 1 wherein the porous silicon substrate comprises porous polysilicon or porous nanocrystalline silicon.

3. The microfluidic system of claim 1 wherein the metal coating comprises gold.

4. The system of claim 1 wherein the metal coating comprises silver, platinum, or aluminum.

5. The microfluidic system of claim 1 wherein the metal coating is formed by contacting the porous silicon substrate with a metal salt solution and heating the porous silicon substrate to form the metal coating on the porous silicon substrate.

6. The microfluidic system of claim 1 wherein the porous silicon substrate has a metal penetration depth of greater than 3 microns.

7. A microfluidic system comprising a porous aluminum substrate wherein the porous aluminum substrate is made electrochemically from a layer of aluminum and wherein the porous aluminum substrate has a metal coating comprising a metal that is not aluminum, a microfluidic pathway wherein the microfluidic pathway is operably coupled to the porous aluminum substrate wherein the microfluidic pathway is capable of allowing a fluid to be delivered to the porous aluminum substrate, and a detection system capable of detecting a change in a region of the porous aluminum substrate comprising the metal coating.

8. The microfluidic system of claim 7 wherein the metal coating comprises gold.

9. The microfluidic system of claim 7 wherein the metal coating comprises silver or platinum.

10. The microfluidic system of claim 7 wherein the metal coating is formed by contacting the porous aluminum substrate with a metal salt solution and heating the porous aluminum substrate to form the metal coating on the porous aluminum substrate.

11. The microfluidic system of claim 7 wherein the porous aluminum substrate has a metal penetration depth of greater than 3 microns.

* * * * *